(12) United States Patent
Riley et al.

(10) Patent No.: US 10,993,841 B2
(45) Date of Patent: May 4, 2021

(54) APPARATUS AND METHOD FOR DYNAMIC FOOT SUPPORT

(71) Applicants: A. Jamie Riley, St. Louis, MO (US); Gary J. Schmidt, St. Louis, MO (US)

(72) Inventors: A. Jamie Riley, St. Louis, MO (US); Gary J. Schmidt, St. Louis, MO (US)

(73) Assignees: A. Jamie Riley, St. Louis, MO (US); Gary J. Schmidt, St. Louis, MO (US)

( * ) Notice: Subject to any disclaimer, the term of this patent is extended or adjusted under 35 U.S.C. 154(b) by 493 days.

(21) Appl. No.: 15/400,577

(22) Filed: Jan. 6, 2017

(65) Prior Publication Data

US 2017/0196737 A1 Jul. 13, 2017

Related U.S. Application Data

(60) Provisional application No. 62/275,923, filed on Jan. 7, 2016.

(51) Int. Cl.
*A61F 13/06* (2006.01)
*A61F 5/01* (2006.01)

(52) U.S. Cl.
CPC .......... *A61F 13/067* (2013.01); *A61F 5/0111* (2013.01)

(58) Field of Classification Search
CPC .... A61F 5/0111; A61F 5/0127; A61F 5/0113; A61F 5/0195; A61F 5/0585; A61F 13/06; A61F 2013/0028; A61F 13/08; A61F 13/067; A61F 13/043; A61F 15/004; A61F 5/019; A61F 13/066; Y10S 2/919; Y10S 2/911; A43B 5/0437; A43B 7/142; A43B 7/143; A43B 7/1495; A43B 23/22; A43B 7/144; A41B 11/02; A41B 11/12; A41D 17/02

See application file for complete search history.

(56) References Cited

U.S. PATENT DOCUMENTS

| | | | | |
|---|---|---|---|---|
| 3,506,000 | A * | 4/1970 | Baker | A61F 13/066 2/22 |
| 4,753,228 | A * | 6/1988 | Selner | A61F 13/066 36/89 |
| 6,350,247 | B2 * | 2/2002 | Bodenschatz | A61F 13/066 128/882 |
| 6,454,733 | B1 * | 9/2002 | Krusenklaus | A61F 13/064 128/882 |
| 6,602,216 | B1 | 8/2003 | Nordt, III | |
| 8,117,770 | B2 | 2/2012 | Wong | |

(Continued)

FOREIGN PATENT DOCUMENTS

DE 393282 C * 4/1924 .......... A61F 13/066
WO 2006068513 A1 6/2006

*Primary Examiner* — Ophelia A Hawthorne
(74) *Attorney, Agent, or Firm* — Sandberg Phoenix & von Gontard, P C.

(57) ABSTRACT

A banded support sock configured to induce a windlass mechanism in a foot includes a sock member having a forefoot portion configured to surround a forefoot of the foot and a heel portion configured to surround a heel of the foot. The banded support sock also includes a primary band having a first end coupled to the forefoot portion of the sock member at a first location, a second end coupled to the forefoot portion of the sock member at a second location, and a body extending between the first end and the second end such that the body extends around the heel portion of the sock member.

20 Claims, 4 Drawing Sheets

(56) References Cited

U.S. PATENT DOCUMENTS

| | | | |
|---|---|---|---|
| 8,663,178 B2 * | 3/2014 | De Luca | A61F 5/019 |
| | | | 2/239 |
| 8,968,229 B2 | 3/2015 | Bushby | |
| 9,320,637 B2 | 4/2016 | Amanatullah | |
| 2015/0018741 A1 * | 1/2015 | Lieberson | A43B 7/144 |
| | | | 602/28 |
| 2016/0100973 A1 | 4/2016 | Nelson | |

* cited by examiner

APPARATUS AND METHOD FOR DYNAMIC FOOT SUPPORT

CROSS REFERENCE TO RELATED APPLICATIONS

This application is a non-provisional and claims priority to U.S. Provisional Patent Application 62/275,923 filed Jan. 7, 2016, which is hereby incorporated by reference in its entirety.

BACKGROUND

The present invention relates generally to support garments and, more particularly, to an apparatus and method for dynamic foot support, using a banded support sock to induce a windlass mechanism in the foot.

The longitudinal arch of the foot, which extends from the heel to the toes, increasingly sags throughout one's lifetime. This sagging may be evidenced by a change in shoe size as the foot elongates over time. Such sagging contributes to foot fatigue, exacerbated arthritis of the foot, and plantar fasciitis. Raising the arch, taking stress off the plantar fascia, or maintaining the arch at an optimal height, improves foot stability and may treat or prevent these issues. At least some known systems attempt to support the arch with orthotics or inserts. The orthotics provide a static upward force on the arch in an attempt to maintain the shape and/or height of the arch. However, such static force is not always successful in providing relief from the above-described problems because the amount of force needed to be therapeutic may be uncomfortable or even intolerable. Some other systems for treating conditions such as plantar fasciitis involve physical therapy systems or methods that may be inaccessible, inconvenient to access, and/or immobile. Moreover, such systems necessarily cannot provide constant, mobile support or relief in one's everyday life.

Therefore, it would be advantageous to provide an apparatus and method that can provide dynamic, comfortable arch support constantly during use and that is accessible and mobile.

BRIEF SUMMARY

In one aspect, a banded support sock configured to induce a windlass mechanism in a foot is provided. The banded support sock includes a sock member having a forefoot portion configured to surround a forefoot of the foot and a heel portion configured to surround a heel of the foot. The banded support sock also includes a primary band having a first end coupled to the forefoot portion of the sock member at a first location, a second end coupled to the forefoot portion of the sock member at a second location, and a body extending between the first end and the second end such that the body extends around the heel portion of the sock member.

BRIEF DESCRIPTION OF THE DRAWINGS

Reference is now made more particularly to the drawings, which illustrate the best presently known mode of carrying out the invention and wherein similar reference characters indicate the same parts throughout the views.

DETAILED DESCRIPTION

In the following detailed description numerous specific details are set forth in order to provide a thorough understanding of the disclosure. However, it will be understood by those skilled in the art that the present disclosure may be practiced without these specific details. For example, the disclosure is not limited in scope to the particular type of industry application depicted in the figures. In other instances, well-known methods, procedures, and components have not been described in detail so as not to obscure the present disclosure.

Figure 1:
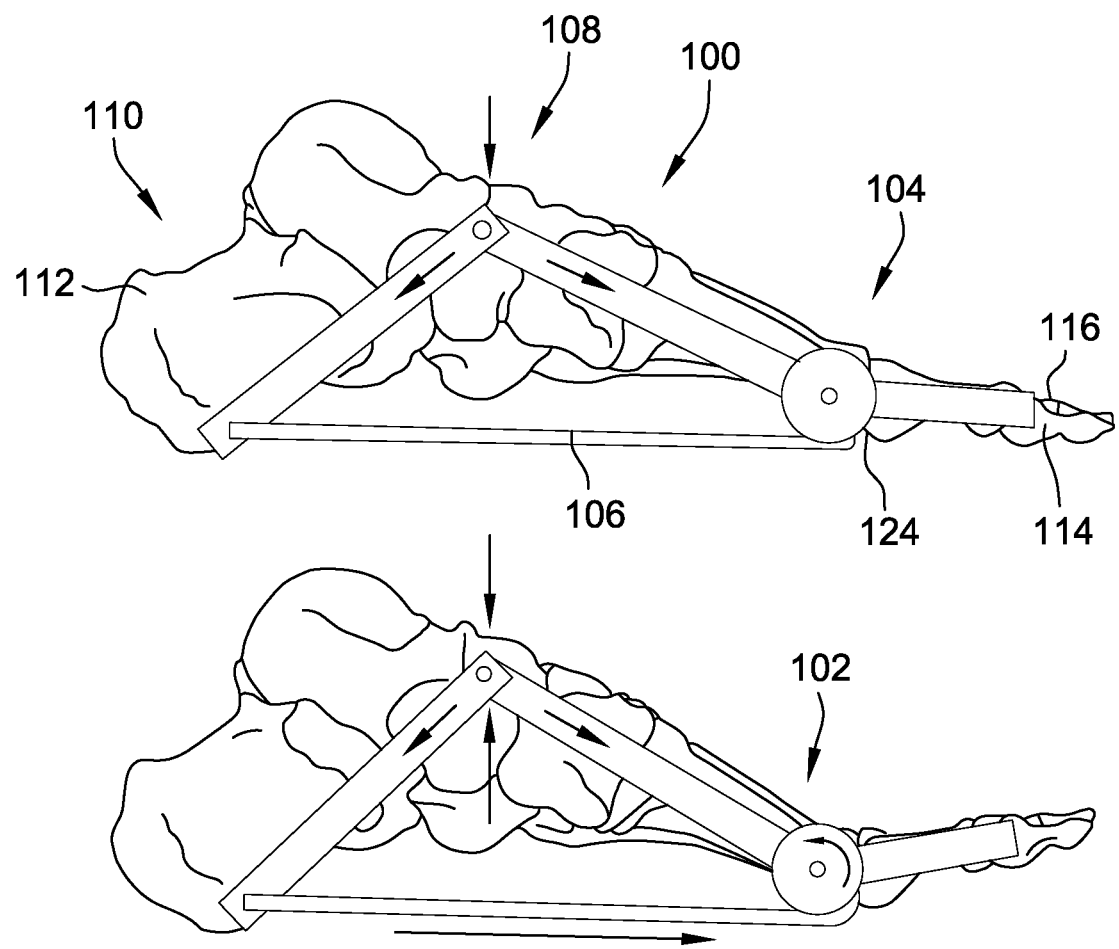
FIG. 1 is a side view of a foot illustrating a windlass mechanism of the foot.
Figure 2:
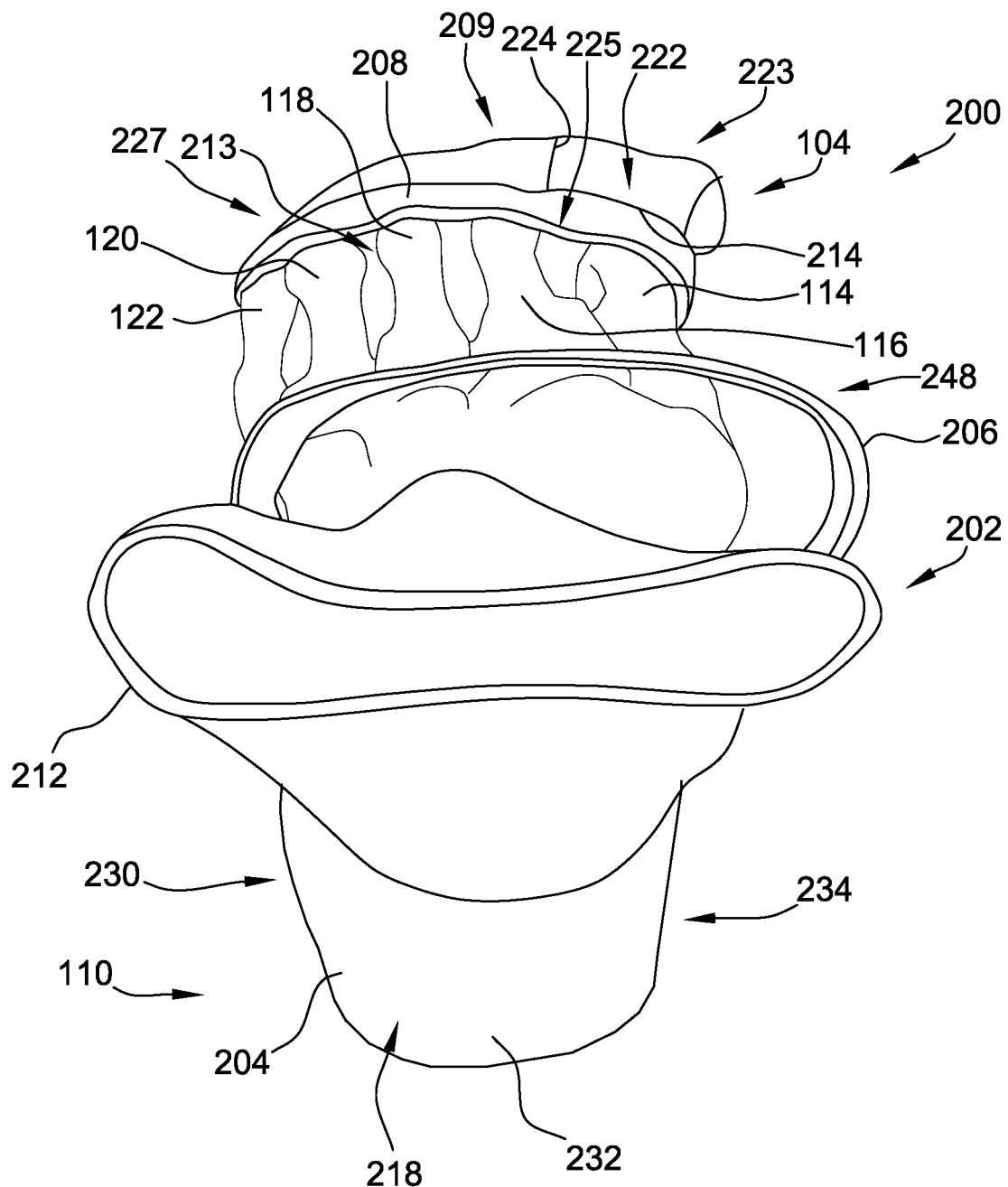
FIG. 2 is top perspective view of an example embodiment of a banded support sock configured to induce the windlass mechanism in the foot, as shown in FIG. 1.
Figure 3:
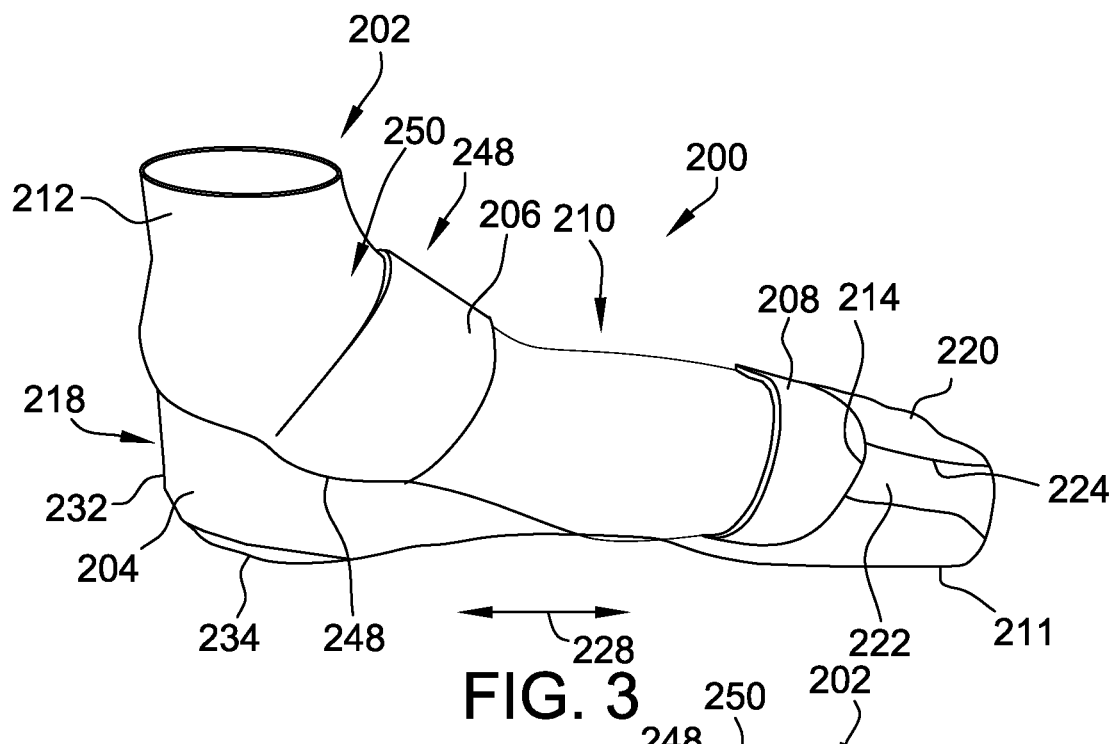
FIG. 3 is a first side view of the banded support sock shown in FIG. 2.
Figure 4:
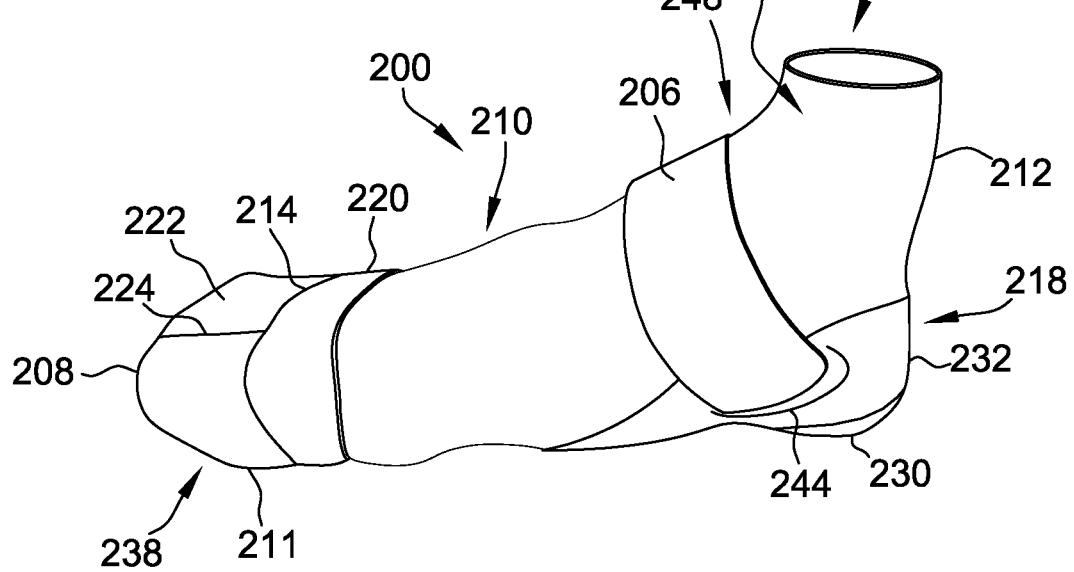
FIG. 4 is a second side view of the banded support sock shown in FIG. 2.
Figure 5:
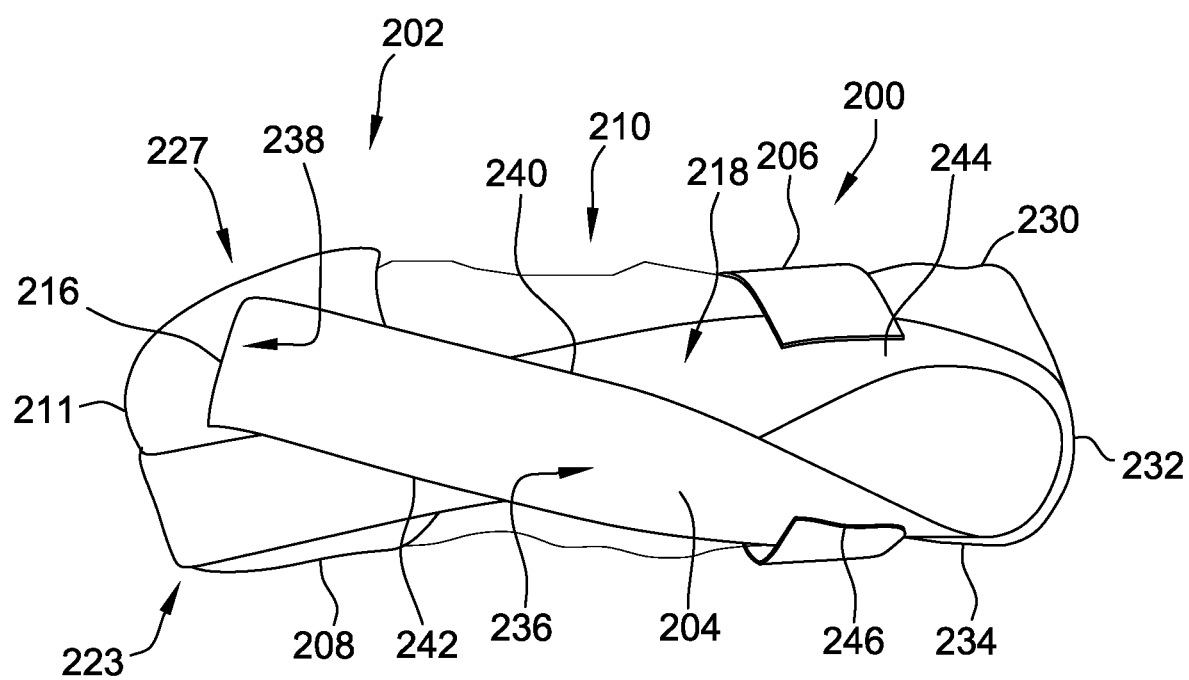
FIG. 5 is a bottom view of the banded support sock shown in FIG. 2.

FIG. 1 is a side view of a foot 100 illustrating a windlass mechanism 102 of foot 100. Foot 100 includes, in pertinent part, a forefoot 104, a plantar fascia 106, and arch or mid-foot 108, and a heel 110 including a calcaneus 112. Forefoot 104 includes a great or first toe 114, a second toe 116, a third toe 118, a fourth toe 120, and a fifth toe 122 (wherein toes 118, 120, and 122 are shown in FIG. 2), and a metatarsal head 124 between each toe 114, 116, 118, 120, 122 and mid-foot 108. Windlass mechanism 102 includes flexing of great toe 114, which winds plantar fascia 106 about metatarsal head 124. Such a pull on plantar fascia 106 in turn induces a forward pull on a calcaneus 112, such that plantar fascia 106 acts as a "tie rod" spanning mid-foot 108 from metatarsal head 124 to calcaneus 112. A distance between each metatarsal head 124 and calcaneus 112 is decreased. Accordingly, dynamic implementation or inducement of windlass mechanism 102 on foot 100, as illustrated, increases a height of mid-foot or arch 108. Moreover, windlass mechanism 102 "packs in" the bones of mid-foot 108 and facilitates locking of mid-foot 108, such that forefoot 104 acts as a more rigid lever for propulsion (e.g., during walking, running, etc.).

FIGS. 2-5 depict various views of a banded support sock 200 configured to dynamically induce windlass mechanism 102 in foot 100. More particularly, banded support sock 200 is a mobile apparatus configured to induce windlass mechanism 102 substantially constantly during wear or use, providing resting compression of foot 100 to lift mid-foot 108 and shorten plantar fascia 106. "Mobile," as used herein, refers to an apparatus configured to be with or on a person regardless of location and/or position, in contrast to an apparatus limited in application to particular locations and/or positions. "Resting compression," as used herein, refers to an application of compression without necessitating action or movement of the person wearing banded support sock 200. For example, "resting compression" occurs while a user of banded support sock 200 is sitting (i.e., no active motion applied to foot 100 by the user).

In the example embodiment, banded support sock 200 includes a sock member 202, a primary band 204, and a support band 206. Sock member 202 is configured to surround at least a portion of foot 100, in the manner of a typical sock. Sock member 202 includes one unitary piece configured to surround an entirety of foot 100 such that at least forefoot portion 208 and heel portion 212 are integrally formed. Alternatively, sock member 202 may include more than one distinct component configured to surround discrete portions of foot 100. For example, forefoot portion 208 and heel portion 212 are separate components coupled together by primary band 204. Sock member 202 may include one or more of a forefoot portion 208, a mid-foot portion that may extend from forefoot portion at a location designated by 210, and a heel portion 212. Forefoot portion 208 includes a top face 209 and a bottom face 211 that define a cavity 213 configured to surround forefoot 104 and to receive a user's toes therein. Mid-foot portion 210 is configured to surround mid-foot 108 and heel portion 212 is configured to surround heel 110. Accordingly, where reference is made to a particular portion 208, 210, 212 of sock member 202, such reference may collectively refer to the corresponding portion of foot 100 (i.e., 104, 108, and 110, respectively) as well.

Sock member 202 is fabricated from typical sock materials, such as cotton, wool, synthetics (e.g., nylon, spandex), silk, and/or combination(s) thereof. Primary band 204 and support band 206 are fabricated from elastic material(s) exhibiting sufficient elasticity to induce windlass mechanism 102 in foot 100. Accordingly, different banded support socks 200 may include bands 204 and/or 206 with different elastic characteristics, such as a stronger elastic band 204 and/or 206 (i.e., having a higher spring constant) for users requiring more elastic force to induce windlass mechanism 102, or a less elastic band 204 and/or 206 (i.e., having a lower spring constant) for users requiring less force to induce windlass mechanism 102. Therefore, primary band 204 provides a high level of control of the elastic force imposed on foot 100 while maintaining the comfort of the user of banded support sock 200.

In addition, in certain embodiments, sock member 202 is integrally formed with primary band 204 and support band 206. In such embodiments, primary band 204 and support band 206 are integrated into of sock member 202 during fabrication thereof, for example, are woven into the weave of sock member 202 or are integrally coupled to the weave of sock member 202. In other embodiments, such as is illustrated in FIGS. 2-5, primary band 204 and support band 206 are discrete components coupled to sock member 202 after sock member 202 is fabricated. It should be understood that wherever "coupled to," "attached to," "joined with," or other similar language is used with reference to sock member 202, primary band 204, and/or support band 206, such language is applicable to any of the above-described embodiment of banded support sock 200.

In the example embodiment, primary band 204 is a continuous band including a first end 214, a second end 216, and a body 218 extending therebetween. First end 214 is coupled to forefoot portion 208 of sock member 202. More specifically, first end 214 of primary band 204 is coupled to top face 209 of forefoot portion 208 at a location 222 proximate a first lateral side 223 of forefoot portion 208 corresponding to great toe 114. Primary band 204 extends from first end 214 on top face 209 around great toe 114 at location 222 and along bottom face 211 such that primary band 204 is coupled to both top and bottom faces 209 and 211 and extends around forefoot portion 208. Location 222 of first end 214 facilitates inducement of dorsiflexion of great toe 114 under the elastic force of primary band 204. Additionally, forefoot portion 208 of sock member 202 includes a seam 224 therein extending between top face 209 and bottom face 211. Seam 224 defines a pocket 225 in cavity 213 and is located in forefoot portion 208 between great toe 114 and second toe 116, or between second toe 116 and third toe 118. Seam 224 defines pocket 225 to retain a respective one of great toe 114, and great toe 114 and second toe 116 therein. Seam 224 and the corresponding pocket 225 ensure that first end 214 of primary band 204 remains in place at location 222, corresponding to great toe 114, preventing slippage of primary band 204 from location 222.

Body 218 of primary band 204 extends around to bottom face 211 of forefoot portion 208 and in a longitudinal direction 228 across mid-foot portion 210 of sock member 202 (or mid-foot 108, in embodiments in which sock member 202 includes no mid-foot portion 210). Body 218 further extends around heel portion 212 of sock member 202, from an outer side face 230 of heel portion 212, across a back face 232 of heel portion 212, to an inner side face 234 of heel portion 212, and is coupled to heel portion 212. Extending body 218 around and securing body 218 to heel portion 212 provides an anchor for primary band 204 and also facilitates establishing an optimal or predetermined amount of force across body 218 of primary band 204. In other words, extending body 218 tighter around heel portion 212 induces a greater amount of force across body 218 than extending body 218 more loosely around heel portion 212.

Body 218 of primary band 204 is then again extended longitudinally across mid-foot portion 210 of sock member 202 (or mid-foot 108, in embodiments in which sock member 202 includes no mid-foot portion 210), specifically in a configuration in which body 218 crosses over itself at a location 236 corresponding to mid-foot or arch 108. Body 204 crosses itself at location 236 corresponding to arch 108 in order to provide maximum compression to arch 108 and plantar fascia 106 threat. In one embodiment, one or more stitches (and/or any other securing elements) are applied to body 218 at location 236 to ensure that body 218 remains crossed over itself at location 236.

Second end 216 of primary band 204 is coupled to bottom face 211 of forefoot portion 208 at a location 238 proximate a second lateral side 227 of forefoot portion 208 corresponding to at least one of third toe 118, fourth toe 120, and fifth toe 122. This securing of second end 216 at location 238 anchors second end 216 of primary band 204 to prevent longitudinal movement thereof and to ensure that primary band 204 retains its predetermined position and configuration, as described herein. It should be understood that primary band 204 may be coupled to sock member 202 at additional locations, for example, along at least a portion of side edges 240, 242 of primary band 204, in order to further ensure that primary band 204 retains its predetermined position and configuration. It should also be understood that the "securing," "coupling," "attaching", and/or other joining described herein may be accomplished using any suitable securing element(s), such as stitches, weaves, hook-and-loop fasteners, adhesives, and/or any combination(s) thereof.

In the exemplary embodiment, extending between first location 222, anchoring surface 232, and second location 238 enables primary band 204 to provide a constant and increasing compressive force between forefoot portion 208 and heel portion 212 that causes the arch or mid-foot to rise and the plantar fascia to shorten, thereby reducing foot stress.

Support band 206 includes a first end 244, a second end 246, and a body 248 extending therebetween. Support band 206 is configured to promote and maintain the configuration of body 218 of primary band 204. Specifically, first end 244 of support band 206 is coupled to outer side face 230 of heel portion 212 of sock member 202, and is coupled to body 218 of primary band 204 located threat. Body 248 of support band 206 extends around a top face 250 of heel portion 212 of sock member 202. Second end 246 of support band 206 is coupled to inner side face 234 of heel portion 212 of sock member 202, and is coupled to body 218 of primary band 204 located thereat. Accordingly, support band 206 prevents body 216 of primary band 204 from slipping off of heel portion 212.

The above-described banded support sock provides an efficient method for inducing the windlass mechanism in a foot. Specifically, the above-described banded support sock is configured such that with dorsiflexion of the great toe of the foot, which, as described herein, the arch or mid-foot rises and the plantar fascia shortens. Moreover, the banded support sock is configured to be accessible and mobile for any user thereof, and provides resting compression of the mid-foot. Accordingly, the banded support sock may reduce foot stress and provide treatment for or relief from chronic foot pain caused by certain foot conditions such as plantar fasciitis or arthritis. The banded support sock described herein is fabricated from materials that enable compression and distraction of the foot on which it is being worn, thereby providing substantially constant and passive support to the foot while maintaining the comfort of the user. User comfort is an important aspect of any therapeutic system, such as the banded support sock, as increased comfort may increase tolerability and therefore usage of the therapeutic system. The banded support sock described herein provides more comfortable arch or mid-foot support for those with chronic pain. Moreover, the banded support sock is configured to actively promote and induce the windlass mechanism for users involved in activities such as running, extended walking, or jumping, which may improve their comfort during such activities and/or may prevent foot injuries caused thereby.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A banded support sock configured to induce a windlass mechanism in a foot, the banded support sock comprising:
   a sock member comprising:
   a forefoot portion configured to surround a forefoot of the foot including at least one metatarsal head and at least one corresponding toe; and
   a heel portion configured to surround a heel of the foot; and a primary band, the primary band comprising:
   a first end coupled to the forefoot portion of the sock member at a first location, the first location configured to be forward of at least one metatarsal head when the banded support sock is worn;
   a second end coupled to the forefoot portion of the sock member at a second location, the second location configured to be forward of at least one metatarsal head when the banded support sock is worn; and
   a body extending between the first end and the second end, the body extending around the heel portion of the sock member.

2. A banded support sock in accordance with claim 1, wherein the forefoot portion of the sock member includes a top surface and a bottom surface coupled together to form a cavity configured to receive a user's toes.

3. A banded support sock in accordance with claim 2, wherein the first end of the primary band is coupled to the top surface of the forefoot portion.

4. A banded support sock in accordance with claim 3, wherein the second end of the primary band is coupled to the bottom surface of the forefoot portion.

5. A banded support sock in accordance with claim 2, wherein the primary band is coupled to the top surface and the bottom surface of the forefoot portion proximate the first end such that the primary band extends around the forefoot portion.

6. A banded support sock in accordance with claim 2, wherein the forefoot portion of the sock member comprises a seam extending between the top surface and the bottom surface adjacent to the first location, the seam forming a pocket in the cavity configured to receive at least the user's great toe and to prevent the first end of the primary band from slipping from the first location.

7. A banded support sock in accordance with claim 1, further comprising a support band configured to prevent the body of the primary band from slipping from the heel portion.

8. A banded support sock in accordance with claim 7,
   wherein the support band comprises a first end, a second end, and a body extending between the first end and the second end,
   wherein the first end of the support band is coupled to the body of the primary band,
   wherein the body of the support band extends around a top surface of the heel portion of the sock member opposite the body of the primary band, and
   wherein the second end of the support band is coupled to the body of the primary band.

9. A banded support sock in accordance with claim 7,
   wherein the support band comprises a first end, a second end, and a body extending between the first end and the second end,
   wherein the first end of the support band is coupled to the heel portion of the sock member,
   wherein the body of the support band extends around a top surface of the heel portion of the sock member opposite the body of the primary band, and
   wherein the second end of the support band is coupled to the heel portion of the sock member.

10. A banded support sock in accordance with claim 1, wherein the primary band is integral to the sock member.

11. A banded support sock in accordance with claim 10, wherein the primary band is woven into the sock member.

12. A banded support sock in accordance with claim 1, wherein the first location comprises a first lateral side of the forefoot portion such that the first lateral side is configured to be positioned adjacent a first end toe of a user when the banded support sock is worn.

13. A banded support sock in accordance with claim 12, wherein the second location comprises an opposing second lateral side of the forefoot portion such that the second lateral side is configured to be positioned adjacent a second end toe of a user when the banded support sock is worn.

14. A banded support sock in accordance with claim 1, wherein the body of the primary band extends in a longitudinal direction along the sock member between the first location and the heel portion.

15. A banded support sock in accordance with claim 1, wherein the body of the primary band extends in a longitudinal direction along the sock member between the heel portion and the second location.

16. A banded support sock in accordance with claim 1, wherein the body crosses over itself between the forefoot portion and the heel portion such that the body is configured to cross over itself adjacent a midfoot portion of the foot of a user when the banded support sock is worn.

17. A banded support sock in accordance with claim 1, wherein the primary band and the sock member are separate components coupled together.

18. A banded support sock in accordance with claim 1, wherein the forefoot portion of the sock member comprises a seam therein adjacent to the first location, the seam defining a pocket configured to receive the great toe and to prevent the first end of the primary band from slipping from the first location.

19. A banded support sock in accordance with claim 1, wherein the forefoot portion and the heel portion of the sock member are integrally formed.

20. A banded support device having a forefoot portion and a heel portion, the banded support device being configured to induce a windlass mechanism in a foot when worn, the banded support device comprising:
 a primary band having a first end, a second end, and a body,
 the first end coupled to the forefoot portion of the device at a first location, the first location configured to be forward of at least one metatarsal head when the banded support sock is worn, the forefoot portion of the device being adapted and configured to engage with at least one metatarsal head and at least one corresponding toe of a foot of a user when the device is worn;
 the second end coupled to the forefoot portion of the device member at a second location; and
 the body extending between the first end and the second end of the device, the body extending around the heel portion of the device such that the body is adapted and configured to engage with a heel of a user when worn,
 wherein the primary band comprises an elastic material and is adapted and configured to provide a compressive longitudinal force between the forefoot portion and the heel portion when the banded support device is worn.

* * * * *